United States Patent [19]

Zaffaroni

[11] 3,998,974
[45] Dec. 21, 1976

[54] COMESTIBLES CONTAINING NON-NUTRITIVE FLAVORING

[75] Inventor: Alejandro Zaffaroni, Atherton, Calif.

[73] Assignee: Dynapol, Palo Alto, Calif.

[22] Filed: June 6, 1975

[21] Appl. No.: 584,550

Related U.S. Application Data

[63] Continuation-in-part of Ser. No. 300,857, Oct. 25, 1972, abandoned.

[52] U.S. Cl. .................................. 426/534; 424/78; 424/80; 424/81; 424/361; 424/362; 424/363; 426/535; 426/536; 426/537; 426/538; 536/3; 536/56; 536/114
[51] Int. Cl.² .......................................... A23L 1/226
[58] Field of Search .................. 260/209 R, 209 D; 426/534–538; 424/78, 80, 81, 361, 362, 363

[56] References Cited

UNITED STATES PATENTS

| 2,596,852 | 5/1952 | Heggie | 426/6 |
|---|---|---|---|
| 3,818,107 | 6/1974 | Yolles | 426/3 |
| 3,876,816 | 4/1975 | Zaffaroni | 426/534 UX |

*Primary Examiner*—Joseph M. Golian
*Attorney, Agent, or Firm*—William H. Benz

[57] ABSTRACT

Nonnutritive flavor imparting compounds of the general formula $(F-Z)_n C$ wherein F is an active flavor imparting agent, C is a controlling agent for transporting and essentially restricting absorption of the compound $(F-Z)_n C$ in a biological environment, Z is a covalent bond for bonding F to C and $n$ is at least one. The nonnutritive flavor imparting compounds are useful for imparting flavor and taste to foods, beverages, confections and medicinals without any substantial absorption of the flavor imparting compounds in the environment of use.

3 Claims, No Drawings

COMESTIBLES CONTAINING NON-NUTRITIVE FLAVORING

This is a continuation-in-part of my related earlier filed U.S. application Ser. No. 300,857 filed Oct. 25, 1972 and now abandoned.

FIELD OF THE INVENTION

The present invention relates to novel and useful compositions of matter and to methods for using same. More particularly, the invention pertains to a new class of compounds useful as flavoring agents for imparting or enhancing the flavor and taste of foods including beverages and confections and also for imparting an acceptable flavor to assorted pharmaceutical formulations. Specifically, the invention concerns nonnutritive flavor imparting compounds comprised of a biologically active flavor imparting agent covalently bonded through a bonding functionality that substantially resists rupture for a prolonged period of time to a molecule having molecular dimensions that substantially prevent absorption of the compounds in a biological environment. The compounds of the invention are useful for imparting flavors to foods, beverages, medicinals and the like, and they can be consumed in safety and without any appreciable absorption or assimilation in the environment of use. The compounds of the invention preferably are water soluble and in use pass through the length of the gastrointestinal tract without degradation and without being absorbed from said gastrointestinal tract into the body of the host.

BACKGROUND OF THE INVENTION

Flavor is an important part of foods including beverages, confections, and other products of commerce. It serves as a primary inducement to man and animals for eating food to concomitantly nourish and sustain themselves. Additionally, for man it gives pleasure and social benefit. To satisfy these purposes, the development of flavor imparting materials that create a sense of satisfaction on the sensory organs of the oral cavity has become the subject of increasing research. This development also arose because of the dual pressing needs for safety-in-use flavor imparting agents to replace those in use that tend to exhibit toxicity or other adverse effects and also for restoring to convenience foods such as instant beverages, deep frozen dishes and dehydrated ready packed meals the flavors lost in the preparation of these foods. Additionally, it is now universally recognized that the use of consumer acceptable flavor imparting agents is essential if the ever increasing world population is to receive flavor attractive and tasty foods.

The present invention makes available a group of flavors which because of their large molecular size in use are not absorbed from the gastrointestinal tract into the body. The present materials are not degraded from their nonabsorbable size during their passage through the gastrointestinal tract. The present materials are soluble in water and aqueous solutions so to permit their use by admixture in the wide range of aqueous based foods, confections and pharmaceuticals which by far make up the majority of materials consumed by man and beast alike.

Applicant is aware of several prior art references which do relate to large-sized flavoring materials.

Applicant's own U.S. Pat. No. 3,876,816 issued on Apr. 8, 1975 and filed of even date with the parent of this application is directed exclusively to nonabsorbable sweetener compounds.

Also of interest is the work carried out with high molecular weight natural protein sweeteners such as the material extracted from the Dioscoreophyllum Cumminsii berry of Nigeria. See for example U.S. Pat. No. 3,826,795 of Essiet issued July 30, 1974. This sweetener initially is of a size which in theory should resist passage from the gastrointestinal tract. However, being proteins, these sweeteners are hydrolyzed at the acid conditions of the stomach to yield small fragments which are absorbed as they pass through the gastrointestinal tract.

Further references are U.S. Pat. No. 2,596,852 issued to Heggie on May 13, 1952; U.S. Pat. No. 3,818,107 issued to Yolles on June 18, 1974; and U.S. Pat. No. 3,826,847 issued to Ogawa et al on July 30, 1974. Each of these references concerns chewing gum. The Heggie reference like the present invention shows flavors chemically bound to large molecules. In the case of Heggie, the large molecules are water insoluble vinyl acetate gums which, while useful in chewing gums, because of their water insolubility do not function in most conventional flavoring applications. The Yolles reference as well shows flavors bound to polymers but expressly requires that the bond between flavor and polymer be easily rupturable so that the flavor moieties be released from the polymers upon mastication of the gum. Thus the flavor moieties would be of an absorbable size as they pass through the gastrointestinal tract. The Ogawa reference shows flavors combined with polymers. This combination is not a chemical one as required herein but rather is a physical dissolving, dispersing or admixing which would not restrict the flavors' absorption.

In view of this presentation, it becomes immediately apparent that a pressing need exists for flavor imparting agents having consumer acceptability with no unwanted effects as frequently associated with the prior art, and that can satisfy the needs and wishes of the user.

OBJECTS OF THE INVENTION

Accordingly, it is an immediate object of this invention to provide a novel compound useful as a flavoring imparting agent, which compound overcomes the disadvantages known to the prior art.

Another important object of the invention is to provide new and improved synthetic chemical food flavor imparting agents of great purity and uniformity that satisfy the user's needs and wishes.

Still another important object of the invention is to provide novel compositions of matter useful for causing a sensation of flavor and taste by stimulating sensory receptors in an oral cavity without any subsequent absorption, metabolism or assimilation of the composition.

Yet still another object of the invention is to provide a nonnutritive, noncaloric, consumer acceptable flavor imparting agent useful for enhancing the palatability of foods, including beverages, confections, animal and avian feeds.

Still a further object of the invention is to make available to the art nonnutritive flavor-like compounds that can be orally ingested, withstand metabolic digestive processes and be eliminated intact from the environment of use.

Yet still a further object of the invention is to provide novel and useful flavor-like compounds that can be used singly or in combination in foods including beverages and confectionaries and in medicinals and feeds.

Yet a further object of the invention is to provide nonnutritive flavor-like compounds that impart flavor to foods or magnify the characteristic taste of foods and can be repeatedly and continuously used in various amounts without any unwanted effects.

Still a further object of the invention is to provide a nonnutritive flavor imparting compound that is inexpensive to manufacture and has acceptable food processing and shelf life.

Yet a further object of the present invention is to provide a nonnutritive flavor imparting agent that can stimulate flavor responsive papillae without causing dental caries.

Other objects, features and advantages of the invention will be more apparent to those skilled in the art from the detailed specification and the accompanying claims.

SUMMARY OF THE INVENTION

This invention concerns nonnutritive flavor imparting compounds comprised of a biologically active agent that can impart a flavor-like response covalently bonded to a molecule that prevents active and passive transport thereof in vivo systems. The active flavor imparting agent is a molecule that can impart or enhance the flavor and taste of food by stimulating oral sense receptors to arouse a corresponding response in animals including humans and avians. The covalent bond, or a functional equivalent thereof, is a bond that is able to withstand metabolic cleavage for a prolonged period of time and it covalently bonds the active agent to the controlling molecule. The controlling molecule is a chemical group or the like whose molecular dimensions substantially prevent the absorption of the nonnutritive flavor imparting compound comprised of said active agent after ingestion by animals including humans. The nonnutritive flavor imparting compounds are soluble in aqueous media and since they are not absorbed in vivo, they inherently eliminate the possibilities of toxicity, unneeded side effects, caloric imput and the like.

DETAILED DESCRIPTION OF THE INVENTION

In accomplishing the objects, features and advantages of this invention, it has now been found that the accomplishments can be fully satisfied by the invention providing in its broadest aspect novel compounds of the following general formula: $(F-Z)_n C$ wherein F is a flavor imparting or enhancing group, Z is a covalent bond, n is at least one, and C is a controlling molecule, with all the terms described hereinafter.

The representation "F" and the expressions "flavor imparting agent", "enhancer" or "modifier" as generally used herein broadly include any substance or chemical group of naturally occurring or synthetic origin capable of producing a flavor effect in animals including humans and avians which can be covalently bonded to C while simultaneously retaining its ability to produce a flavor imparting effect. In the compound $(F-Z)_n C$ there is at least one F covalently bonded to C; however, the invenion also includes embodiments of more than one F bonded to C, such as 1 to 10,000 and higher, or the like. The result obtained for the flavor imparting compounds of the invention are conventionally identified as "fruit-like", "spice-like", "nut-like", "grain-like", "pepper-like", "sour-like" and the like. The flavor imparting active group can be covalently bonded directly or through other functionally equivalent covalent bonding moieties attached to the active flavor imparting group that are not essential for its intended effect. The active flavor imparting group can have an inherent nutritive value which is not available to a user because the active group is covalently bonded to the controller molecule C. Generically, the active agent can be any group that causes flavor, imparts, enhances or modifies the flavor and/or taste of food, beverages, confections, medicaments and the like, without making other inherent properties available for entering into the systemic system because of its intimate union with the controller molecule that retains the compound in the gastrointestinal tract.

The flavor imparting active agents F suitable for forming the novel compound $(F-Z)_n C$ of the invention are those agents that can be added to foods, beverages and the like, found in all regions of the world. These flavor imparting agents include aliphatic aromatics, heterocyclics, and other compounds with different chemical structures such as alkaloids, terpene hydrocarbons, amides, oximes, benzenoids, fused rings, esters, ethers, acids and other organically structure flavor imparting agents. Typical flavor imparting agents with their flavor-like properties are as follows:

Allyl anthranilate

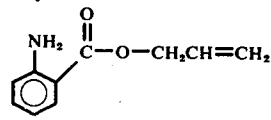

Grape-like flavor

Isoestragole

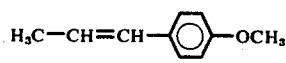

Anise-like flavor

Benzyl-3-phenylpropenoate

Isovaleric acid, ammonium salt

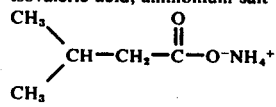

Cheese-like flavor

Phenylmercaptan

Garlic-like flavor

Benzyl-O-hydroxybenzoate

-continued

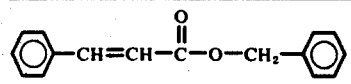   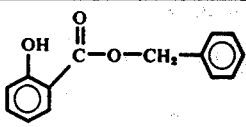

Honey-like flavor

Butyl anthranilate

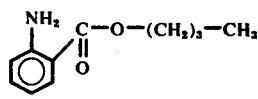

Plum-like flavor

Cinnamyl-o-aminobenzoate

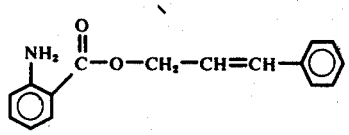

Grape-like flavor

Cinnamyl isovalerate

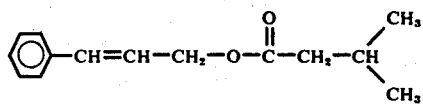

Apple-like flavor 1,2-Benzopyrone

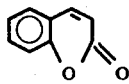

Nut-like flavor

Ethyl anthranilate

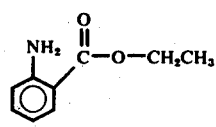

Orange-like flavor

Ethyl vanillin

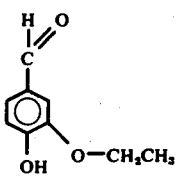

Vanilla-like flavor

O-Methoxycinnamaldehyde

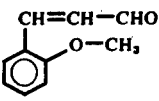

Currant-like flavor

Trans-cinnamic acid

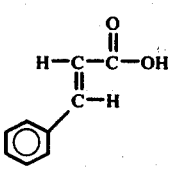

Apricot-like flavor

Phenyl propenyl-n-butyrate

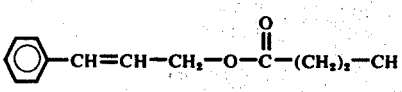

Honey-like flavor

Cinnamyl α-toluate

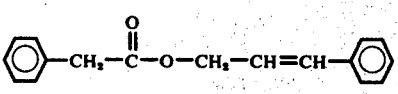

Honey-like flavor

Cyclohexyl anthranilate

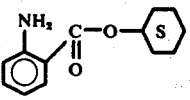

Grape-like flavor

Ethyl 3-phenyl-3-oxopropanoate

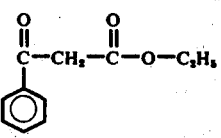

Whiskey-like flavor 3,7-Dimethyl-1,6-octadien-3-yl-anthranilate

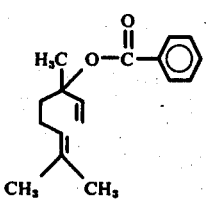

Orange-like flavor 1-(p-Methoxyphenyl)-1-penten-3-one

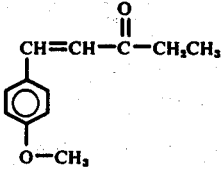

-continued

Spicy-like flavor

Methyl anisate

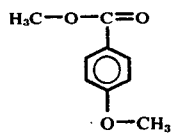

Melon-like flavor

3-Methylcyclopentan-1,2-dione

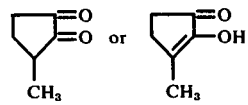

Licorice-like flavor

Methyl β-naphthyl ketone

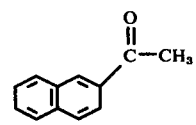

Strawberry-like flavor

Phenylethyl β-phenylacrylate

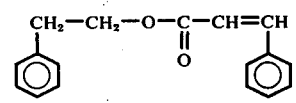

Plum-like flavor

Hydrocinnamic acid

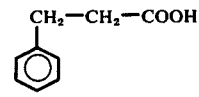

Vanilla-like flavor p-Cresyl phenylacetate

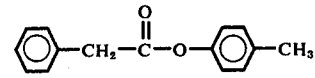

Honey-like flavor

Veratraldehyde

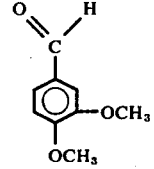

Vanilla-like flavor

Sedanolide

Fruity-like flavor

Methyl-3-phenyl propenoate

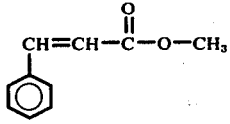

Strawberry-like flavor

Methyl-n-methylanthranilate

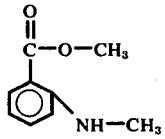

Berry-like flavor

Methyl pelargonate

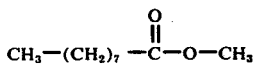

Coconut-like flavor

Phenylium

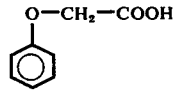

Honey-like flavor

Propenylguaethol

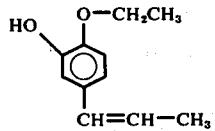

Vanilla-like flavor

Protocatechualdehyde-3 methyl ether

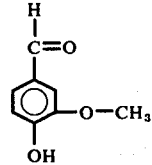

Vanilla-like flavor

Benzyl carbinyl salicylate

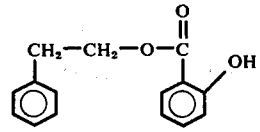

Peach-like flavor

γ-Methylmercaptopropylalcohol

| | |
|---|---|
| CH₃(CH₂)₃ 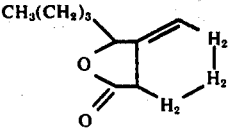 | CH₃S . CH₂CH₂CH₂OH |
| Celery-like flavor | Soy-like flavor |
| Ethyl ester of 2,4-decadienoic acid | Pyrazine derivatives where X is oxygen or sulfur |
| CH₃(CH₂)₄CH:CHCH:CHCOOC₂H₅ | 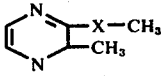 |
| Pear-like flavor | Nut-like flavor |
| Isopropylthiazolidine | Isobutylthiazolidines |
| 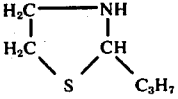 | 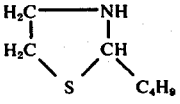 |
| Chocolate-like flavor | Chocolate-like flavor |
| Substituted aldimines where R is branched alkyl of 3 to 6 carbons | Piperine |
| 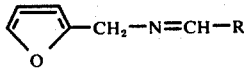 | 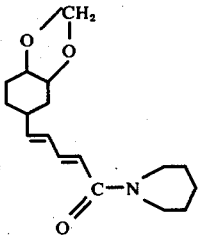 |
| Chocolate like flavor | Pepper-like flavor, and other like agents. |

The letter "Z" as used for the purpose of the invention broadly includes a covalent bond or a covalent bonding group that effectively joins the active flavor imparting group F to C to form the novel, nonnutritive flavor imparting compound (F—Z)ₙC wherein n is at least one. Usually, for each F group there is at least one covalent bond. The invention also includes embodiments comprised of an active F group covalently bonded through more than one position on the F group to at least one position or more than one position on C. The covalent bond or an equivalent thereof is at least 1, or from 1 to 10,000, or higher. Generally, the covalent bond or a functional equivalent thereof includes any bond that can couple the active F to C and substantially resist rupture when mixed into assorted items of commerce, can resist thermal rupture at baking and culinary temperatures, on storage and can essentially resist acidic hydrolysis and enzymatic cleavage during passage of the compound through the gastrointestinal tract of animals including humans and also avians. By a prolonged period of time, as used herein, is broadly meant that the novel flavor imparting compounds (F—Z)ₙC are able to maintain their physico-chemical integrity for a period of time range from about 12 hours or less to 3 years or longer. The active group F is joined by a covalent bond or its equivalent to C through at least one position or substituent on the flavor imparting group F that substantially does not interfere with its flavor imparting properties. The C group of the novel flavor imparting compound (F—Z)ₙC, as will be discussed later in this disclosure, is a constricting group that has a molecular shape or molecular weight and shape that prevents in vivo absorption of itself, and the F group as bonded thereto. Thus, the flavor imparting compound (F—Z)ₙC is essentially nonabsorbed and nonassimilated in its passage through the gastrointestinal tract of the user.

Generically, the bonding expression Z includes a member selected from the group consisting of a single covalent bond; a straight chain divalent alkylene bridge $-(CH_2)_n-$ wherein n is 1 to 18; a branched or substituted divalent alkylene bridge of the formula $-(CR_1R_2)_y-$ wherein $R_1$ and $R_2$ are the same or different and they are selected from the group consisting of hydrogen, lower alkyl, lower alkoxy, lower alkenyl, hydroxyl, aryl and halogen with the proviso that at least one of $R_1$ and $R_2$ or both are other than hydrogen and y is 1 to 12 and they are the same or different; a lower alkenyl bridge —CH=CH—; a lower alkyne —C ≡ C—; an oxa linkage —O—; a carbonyldioxy

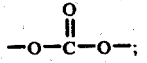

an acyl linkage

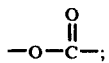

an amide function

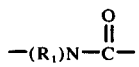

wherein $R_1$ is the same as $R_1$ and $R_2$ above; an azo linkage —N=N—; an alkylenedioxy of the formula —O$(CR_1R_2)_y$O— wherein $y$ is as defined and $R_1 = R_2 =$ hydrogen or any of the above as defined for $R_1$ and $R_2$; an alkenyldioxy bridge —O$(CH=CH)_p$O—, wherein $p$ is 1 to 4; an alkyleneoxa linkage —O$(CR_1R_2)_y$ wherein $y$, R and $R_2$ are as defined; a straight chain azalkylene $(CH_2)_p$NH$(CH_2)_p$, as well as $(CH_2)_p$N=CH$(CH_2)_p$ wherein $p$ is 1 to 4; a thialkylene $(CH_2)_p$S$(CH_2)_p$ wherein $p$ is 1 to 4 and oxidized forms thereof such as sulfoxide and sulfone; an oxalkylene $(CH_2)_p$O$(CH_2)_p$, a bivalent aromatic radical such as arylene

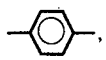

and a bivalent aralkylene

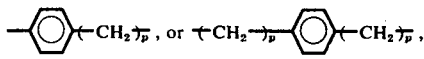

wherein $p$ is 1 to a divalent cycloalkylene

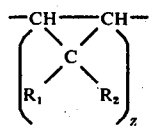

wherein 2 is from 1 to 4; an alkylene oxide

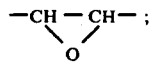

a divalent or six membered heterocyclic radical wherein the radical is a thiocyclic, an oxacylic; a monazacyclic, diazacyclic or a triazacyclic that can be optionally substituted or unsubstituted; and like covalent bonding functions. Additionally, the invention embraces combinations and mixtures of the above expressions.

Typical of the straight chain divalent alkylene $(CH_2)_n$ radicals wherein $n$ is 1 to 18 suitable for the present purpose include methylene, ethylene, propylene, butylene, hexamethylene, octamethylene, nonomethylene, decamethylene undecamethylene, dodecamethylene, tetradecamethylene, hexadecamethylene, heptadecamethylene and octadecamethylene. Representative of lower alkyl R groups substituted onto the unit $(CR_1R_2)_y$ include lower alkyl groups of 1 to 7 carbons including the straight and branched chain alkyl groups such as methyl, ethyl, n-propyl, n-butyl, n-amyl, isopropyl, isobutyl, t-butyl, sec-butyl, isoamyl, t-amyl, isohexyl and the like. Exemplary lower alkenyl R's of 1 to 7 carbon atoms include ethenyl, 1-propenyl, allyl, 1-butenyl, 3-butenyl and the corresponding isomers thereof, such as 1-isobutenyl, 1-sec-butenyl, 1-pentenyl, 2-methyl-1-butenyl, 1,1-dimethyl-2-propenyl and the like. Representative lower alkoxy R's include methoxy, ethoxy, isoporopoxy, butoxy, and the like.

Typical divalent covalent bonding alkylene groups $(CR_1R_2)_y$ substituted with the above substituents include 1,1-dimethylmethylene, 1,1-dimethylethylene, 2-methylpropylene, 1-methoxymethylene, 2-ethoxypropylene, 3-methoxyhexamethylene, 4-isopropyloctylene, 2-allylpropylene, 2-butenyl-1-butylene and the like. Representative of divalent alkenylene groups having 2 to 7 carbon atoms include 1-propenylene, 2-butenylene, 2-pentenylene, 2-propenylene, 2-methyl-2-butenylene, ethenylene, 1-heptenylene, and the like. representative of divalent lower alkynene covalent bonding groups include groups of 2 to 7 carbon atoms including ethynylene, 2-propynylene, 2-penten-4-ynylene, 2-butynylene, 2-pentenediylidyne, and the like.

The term alkylenedioxy as a divalent linkage as used herein includes the group methylenedioxy, ethylenedioxy, enedioxy, propylendioxy, butylenedioxy, hexylenedioxy and the like. The term alkenyldioxy includes ethenylenedioxy, 1-propenylenedioxy, 2-propenylenedioxy, isopropenylenedioxy, 1-butenylenedioxy, and the like. Representative of azalkylene, thialkylene, and oxalkylene include symmetrical, (sym) and unsymmetrical, (unsym), moieties such as sym-azadimethylene, sym-azadiethylene, sym-azadipropylene sym-thiadiethylene, sym-thiadipropylene, sym-oxadimethylene, unsym-oxamethylene and the like. Typical examples of arylene and aralkylene include phenylene, sym-phenyldimethylene, sym-phenyldiethylene, sym-phenylisopropylene, and the like.

The term divalent cycloalkylene as used herein includes lower cycloalkyl radicals having three to seven ring carbon atoms as illustrated by disubstituted cyclopropyl, cyclobutyl, cyclopentyl, cyclohexyl, cycloheptyl and the like. Representative of alkylene oxide are ethylene oxide and propylene oxide.

The expression "a divalent five or six membered heterocyclic radical having an oxa, aza or thia member" includes heterocyclic radicals having two positions suitable for forming covalent bonds with one position covalently bonded to F and the other to C. Exemplary heterocyclic radicals are 2,5-thiazolyl, 3,4-furyl, 1,4-pyrazinyl, 3,4-pyrrolyl, 3,5-pyranyl, 3,5-piperidyl, 3,4-pyrazolidnyl, and the like. These, and other covalent bonding groups that essentially maintain their original bonding integrity in vitro or in vivo can be used for the purpose of the invention. The covalent bonding group also includes those groups that maintain their bondality even with various substituents attached to the parent group. This includes substituents that may be altered, changed or reacted with other groups in the environment of use so long as the covalent bond between F and C is maintained for a prolonged period of time.

The group C, as used for the purpose of the present invention, is comprised of a moiety that has F covalently bonded thereto. In operation, C serves to both confine F within a commodity and to transport it through the gastrointestinal tract of animals, humans or avians without any substantial absorption of $(F—Z)_n$C. The group C can be classified as a controlling group or a controller molecule because its dimensions, in size or shape or both, restrict the movement of $(F-Z)_nC$ across the wall of the digestive tract. That is, C's dimensions essentially prevent active or passive absorption of F through the gastrointestinal wall into the systemic circulation so that C is always external to the body even when $(F-Z)_nC$ is present in the gastrointestinal tract of the user.

Group C can be a naturally occurring or synthetic material and it can have either hydrophilic or hydrophobic properties and it is preferably a material that maintains its physical and chemical integrity in the environment of use. That is, it is essentially nonmetabolizable, nonbiodegradable, indigestable and the like in the gastrointestinal tract. The novel nonnutritive flavor imparting compound $(F-Z)_nC$ can also be substituted with conventional groups that impart various aqueous solubilities to accommodate its presence in an assortment of edible commodities and in the environment of use. Generically, C's dimensions include any chemical moiety that prevents absorption of the flavoring agent F by biological absorption mechanisms, such as passive transport, osmosis, active transport including pinocytosis and phagocytosis. Generally, C is comprised of at least one three dimensional space occupying group, that is, having at least one nonplanar atom or other groups with dimensions such that the total molecular volume of C in any one of its three dimensions substantially restricts its movement from the mucosal to the serosal side of the digestive tract. That is, the space occupied by C is always sufficiently larger than the transport pathways of the gastrointestinal tract. This embodiment of the invention substantially prevents absorption of the active molecule into the systemic system and also eliminates the likelihood of caloric input and unwanted toxicity from any component of the compound. The controlling molecule C should have a molecular weight in excess of 400 with a presently preferred molecular weight in excess of 1000, usually in the range of 1,000 to 2,500,000 or more to substantially prevent any penetration into cells or microvilli or pores and the like of the gastrointestinal tract. The nonnutritive flavor imparting compounds prepared according to the mode and manner of the invention should have a molecular weight in excess of 500 and preferably have a total molecular weight in excess of 1000, usually in the range of from 1000 to 250,000. and they also have essentially a zero rate of movement from the mucosal to the serosal side of the gastrointestinal tract.

Exemplary materials suitable for use as the controller molecule C include polymer and polymeric-like materials of naturally occurring and synthetic origin, and materials fabricated of the F moiety itself. When F is also C it can have polymeric forms as the oligomer, such as the dimer, trimer, tetramer, heptamer, octoamer and the like. The materials comprising C can have a linear or branched structure, they can be cross-linked and substituted or unsubstituted. The C materials suitable for the present purpose are those that are essentially indigestible for a prolonged period of time, that is, for a time sufficient to pass through the gastrointestinal tract of the user, generally about 10 hours or less to 36 hours or longer. Generically, the natural polymeric and oligomeric materials include exudates from vegetation, seed extracts, seaweed products, polymers of animal origin, and the like. The synthetic polymeric and oligomeric materials include homopolymers and copolymers synthesized by condensation polymerization, addition polymerization such as free radical polymerization, and like techniques.

Exemplary polymeric materials suitable for the present purpose include the commercially available celluloses conventionally produced by reacting cellulose with an alkali to yield alkali cellulose, by reacting an alkali cellulose with an alkyl halide to yield alkylcellulose, by reacting an alkali cellulose with an alkylene oxide to yield a hydroxyalkylcellulose, and the like. Typical cellulose polymers resistant to depolymerization or degradation include cellulose, methylcellulose, hydroxypropylmethylcellulose, ethylcellulose, ethylhydroxyethylcellulose, ethylmethylcellulose, hydroxyethylcellulose, hydroxyethylmethylcellulose, sodium carboxymethylcellulose, sodium carboxymethylhydroxyethylcellulose and the like. Typical naturally occurring products include agar-agar agarose, algin and alginates, propyleneglycol alginate, sodium alginate, Irish moss, fucoidan, acylated fucoidan, laminarian, hypnean, furcellaran, iridophycan, gum tragacanth, corn hull gum, dextran and like natural products. Exemplary synthetic polymeric materials suitable for the purpose of the invention include carboxyvinylpolymers, polyvinylalcohol, polyethylene glycol, polypropylene glycol, polyethylene oxide, polyethylene sorbitan tristearate, polyvinylpyrrolidone, polysorbate and other materials that are metabolized only after a prolonged period of time. Representative of the latter materials include polyacrylamides, modified polyacrylamides, acrylamid-acrylic acid co-polymers, cross-linked medium weight nonbiodegradable polymeric polyacrylamides, and the like. Exemplary oligomers are compounds of the formula $(F-Z)_\pi C$ wherein F is C, to give $(F-Z)_\pi F$, that is, an oligomeric material comprised of at least one F group covalently bonded to one or more like or unlike F groups to form the novel oligomer $F(F)_pF$, wherein $p$ is 0 to 25,000 and F is any of the active groups described supra. The materials for either of the above, that is, a polymer or oligomeric material can be used in the forms of acceptable derivatives such as ethers, acid addition salts, amides and the like that freely lend themselves to controlling the solubility of the material for enhancing the use of the compound in both the user and in commercial articles of manufacture.

The compounds of the invention, $(F-Z)_\pi C$, can be synthesized by conventional methods well known to the art. The group F may be covalently bonded through any position or substituting group on F that does not interfere with its ability to act as a flavor imparting group. The conventional methods suitable for synthesizing the novel and useful compounds includes nucleophilic substitution displacement reactions of the following general equation (a) $R-O^-M^+ + R'X \rightarrow R-O-R' + X^-M^+$ wherein R is a polymeric backbone, M is a cation, R' is a flavor imparting moiety and X is a leaving group. Optionally, the reverse conditions wherein R is a flavor imparting group and R' is a polymeric type reactant can also be used to synthesize the product. The nucleophilic substitution also includes the general reaction (b),

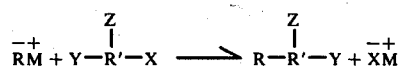

wherein R is a polymeric reactant, M is a cation, R' is a flavor imparting group, Y is any substituent, Z is a hetero atom and X is a leaving group. As above, the nucleophilic substitution also includes the reverse conditions thereof.

The compounds can also be synthesized by nucleophilic addition or coupling reactions such as (c),

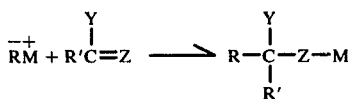

wherein R is a polymer, M is a cation, R' is a flavor imparting group, Y is any substituent such as hydrogen, alkyl and the like and Z is a hetero atom such as oxygen, nitrogen or sulfur, and by the addition reaction (d),

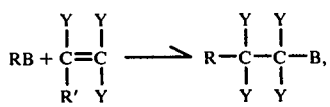

wherein the groups are as defined except that B is a functional group containing a partial charge and is optionally associated with R, and wherein optionally the reverse reaction conditions can be used to yield the product. The product can also be synthesized by electrophilic addition or coupling reactions such as (e),

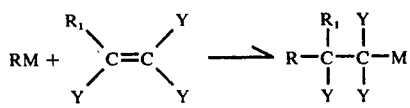

and (f),

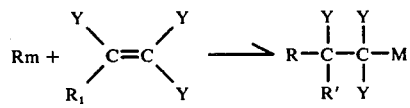

in a single stage or two stage reaction wherein the terms are as defined and M is now an anion, and by electrophilic substitution or displacement reactions such as (g),

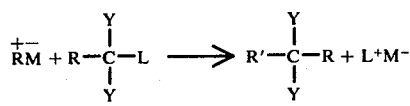

wherein the terms are as defined. These methods of synthesis are described in Organic Chemistry, by Cram, D. J. and Hammond, G. S., Second Edition, Chapters 13, 15 and 17 through 20, published by McGraw-Hill Co., New York. Another operable method suitable for the present invention is the free radical coupling reaction. This method is comprised of irradiating a high molecular weight organic polymeric material having hydrogen atoms with ultra violet light for a period of time sufficient to form a reactive center and simultaneously contacting the polymer with an unsaturated flavor imparting compound having a reactive site to form the desired product.

Typical examples for bonding the flavor imparting group to the polymeric structure include reacting a group having at least one hydroxyl or amino group with a cyanogen halide and with a polymer having similar functional groups under mild alkaline conditions at 0 to 50° C for a time sufficient to yield the desired product. Another method is comprised of exposing a polymer to beta or gamma rays, accelerated particles or the like to form active centers on, for example, cellulose or the like, to which center an active flavor imparting moiety is bonded thereto. Another representative method for forming the compound is comprised of reacting a synthetic polymer such as dextran with a triazinyl substituted with both a halogen that reacts with the polymer and a nucleophilic substituent that reacts with a reactive functionality of the flavor imparting groups. Additionally, the flavor imparting group can be bonded to the polymer by conventional processes such as diazotization, by reacting an acyl halide, a carboxyl or anhydride group of a polymer with an amino, hydroxyl or sulfhydryl group integral with or bonded to a flavor imparting group in aqueous buffer media, inert organic or mixed solvents; by introducing oxirane groups into hydrophilic polymers such as the polysaccharides agarose, cellulose, sephadex, or dextran, cross-linked polyhydric alcohols, soluble and nondegradable polyacrylic acids, polyacrylamides, or their derivatives and then coupling the now activated polymers with a biologically active flavor imparting agent having at least one reactive amino, imino, alcoholic, alkoxy, alkenyl or other functionality to produce the products of the invention wherein the flavor imparting agent retains its original activity completely or in part.

The covalent attachment of the flavor imparting agent to the polymer can also be efficiently and effectively carried out by the reaction of an alkoxide anion, either as a functionality of the flavor imparting molecule or the polymer reactant with an oxiran ring or leaving group such as a toluenesulfonate ester, which latter groups are part of the other reactant. Specifically, these methods comprise reacting the alkoxide anion functionality of the polymer with the oxirane ring or leaving group on the flavor imparting molecule or conversely by reacting the alkoxide anion functionality of the flavor imparting molecule with the oxirane ring or leaving group of the polymer. The compound can also be synthesized by the combination of a 1,2-diol or a 1,3-diol with an aldehyde (acetalization), or ketone (ketalization), wherein the diol function can be part of the flavor molecule or polymer and the aldehyde or ketone functionality part of the alternate reactant. Other means for forming covalent bonds such as thioesters, disulfides, amides, imides, esters and the like can be readily formed by reacting for example a pendant carboxyl group of a flavor imparting molecule with a hydroxyl, amine, mercaptan group or the like on the other reactant, wherein activation of a carboxyl group can be effected by the reaction of the carboxyl group with various carbodiimides, carbodimidazoles, Woodward's reagent and the like to form highly active intermediates capable of reacting with other groups mentioned above in the presence of a solvent and under mild reaction conditions to yield the desired compounds.

An alternative procedure for preparing $(F-Z)_{\overline{m}}C$ consists in using F as a monomer which can be copolymerized with a different monomer to yield a nonabsorbable copolymer in which the F moiety functions as a flavor imparting agent while remaining an integral part of the copolymer.

In another embodiment, the nonnutritive flavor imparting compound can be synthesized as an oligomer comprised of individual F moieties covalently bonded to each other thusly F(F)$_p$F wherein $p$ is 0 to 25,000. In this embodiment at least one or all of the F moieties can produce a flavoring effect while simultaneously remaining an integral component of the oligomer.

The reactions used for synthesizing the desired products and intermediate compounds used for producing the desired products are conventional reactions. These reactions are usually carried out by intimately contacting and reacting the reactants optionally in the presence of a solvent for a time sufficient for them to react, usually about 15 minutes to 96 hours or longer at reaction temperatures of about 0° C or less to 100° C or higher, and usually at room temperature of about 25° C or at slightly elevated temperatures. Generally, stoichiometric amounts or an excess thereof are reacted under normal atmospheric pressure or at pressures up to 10 atmospheres to produce from the starting reactants the corresponding products. The product is recovered from the reaction vessel by procedures such as the evaporation of the aqueous or organic solvents, by the addition of miscible solvents of low polarity, by chilling the mixture to precipitate the product, and the like.

Exemplary of suitable solvents, in its broadest context, are solvents suitable for the coupling of the flavoring imparting group to the polymer either directly or indirectly through use of an activating agent without adversely effecting the purpose of the polymer group. The solvent used by those versed in the art in the light of the specification for the purpose of the invention can be an inorganic, organic or mixed solvent such as water, organic solvents in combination with water, an aqueous buffer, organic solvents such as halogenated solvents like methylene chloride, chloroform and ethylene dichloride, and other solvents such as pyridine, tetrahydrofuran, dioxane, diethylether, dimethylether, benzene, dimethylsulfoxide, methylene dichloride, carbon tetrachloride, cyclopentane, cyclooctane, n-hexane, n-heptane, isobutyl ketone, dimethylforanamide, ether benzene mixtures, and the like. The amount of solvent used is an amount sufficient to partially or completely solvate interacted sites of the reactants and thus enhance the ability of the preselected functional group to react and produce the product.

Representative of acid catalysts suitable for performing the reaction when required herein are p-toluenesulfonic acid, hydrochloric acid, anhydrous hydrobionic acid, Lewis acids such as boron trifluoride, aluminum chloride boron, trichloride etherate, boron trifluoride etherate, stannic oxychloride, phosphorous oxychloride, phosphorous pentachloride, zinc chloride, zinc oxide, and the like.

The esterification of a carboxyl group on a polymer or on a flavor imparting agent as a means for controlling the solubility of the compound of the invention is obtained by standard chemical techniques. These techniques consist of reacting a carboxyl group with a solution containing a diazoalkane or the like to produce the ester. Esterification of the acid group is performed by reacting the group with a diazoalkane, for example, diazomethane, diazoethane, diazopropane, diazobutane, etc., in an inert organic solvent, for example, symmetrical and unsymmetrical ethers, halogenated solvents or mixtures thereof. The esterification reaction is usually performed at a temperature of 0° to 75° C, usually at room temperature and atmospheric pressure, with the ester recovered by evaporation of the solvent and like techniques. The esterification reaction is described in Organic Chemistry, by Fieser and Fieser, pages 180 to 181, 1944.

The compounds of the invention bearing a basic group, such as amino or the like, can be converted to non-toxic acid addition salts having improved aqueous solubility to enhance their use in foods, beverages and medicines. Although non-toxic salts are prepared, any salt may be prepared for use as an intermediate in the preparation of another but non-toxic acid addition salt. The free basic group can be conveniently converted to the acid addition salt by reacting the base with the selected acid by the customary methods such as by dissolving the free base in a suitable inorganic or organic solvent inert to the reactants and reaction products and acidifying the solution with the desired acid. The acids which can be used to prepare the salt are preferably the acids that form non-toxic acid addition salts including organic and inorganic acids such as hydrochloric, hydrobromic, hydroiodic, nitric, sulfuric, phosphoric, acetic, lactic, fumaric, tartaric, glycolic, maleic, succinic, salicylic and the like. The acid addition salt is recovered by conventional methods such as evaporation of the solvent, filtering, freezing, crystallization and the like.

The nonnutritive flavor imparting compounds and intermediates used to prepare same when bearing at least one carboxyl functionality can also be used in the form of their base addition salts that have improved solubilities in aqueous media and other carrier systems. These salts include alkali metal and alkaline earth bases such as sodium, potassium, calcium, copper and magnesium, the hydroxides and carbonates thereof, the ammonium salts and substituted ammonium salts, salts of alkylamines such as triethylamine, trimethylamine, triisopropylamine, methylcyclohexylamine, N-(lower) alkyl piperidines and the like. Also, salts formed from compounds like tetraalkylammonium hydroxides which are known as quaternary ammonium salts. The salts are prepared by procedures known to the art, for example, equivalent or stoichiometric amounts of the free carboxyl compound and the organic base are dissolved in an inert, inorganic or organic solvent followed by slowly warming the solvent with gentle mixing of the reactants. The product or salt is then obtained by chilling the resulting mixture to precipitate the salt, powder or crystals. The product can be recovered by the addition of a miscible diluent of low polarity, or by the use of standard evaporation techniques. The formation of the inorganic salts is also carried out by procedures known to the art; for example, the free carboxyl group is first dissolved in a solution containing stoichiometric amounts or an excess amount of a salt forming inorganic hydroxide, carbonate or the like. The reaction is carried out in a solvent and the product isolated by procedures such as the evaporation of the solvent, chilling to precipitate the product and like techniques.

The solubilities of the nonnutritive flavor imparting compounds, or of intermediates leading thereto, also can be regulated by acylating the free hydroxyl group of the compound or the polymer or both. Exemplary of acyl derivatives acceptable herein include acyl derivatives of the hydroxyl groups where the acyls have 1 to 18 carbons such as alkanoyl, alkenoyl, aroyl and the like. Typical alkanoyl groups include formyl, valeryl, acetyl, propionyl, heptanoyl, octanoyl, undecanoyl, lauroyl, palmitoyl, stearoyl, oleoyl, isomeric forms thereof and the like; typical alkenoyl groups include acryloyl, methacryloyl, crotonyl, 3-butenyl, β-methyl-α-butenoyl, and the like; typical aroyl groups are benzoyl, phenylacetyl, cinnamoyl, naphthoyl, p-ethoxybenzyl, allyloxyphenylacetyl, and the like. Exemplary of other acyl moieties within the scope of the invention are carboxacyl, moieties such as cyclohexanecarbonyl, 3-cyclohexanecarbonyl, p-chlorophenoxyacetyl, succinyl, p-nitrobenzoyl, furoyl, 3-pyridinecarbonyl, and the like.

The acylation is advantageously carried out by mixing the free hydroxyl compound with an acid anhydride usually in the presence of an amine solvent. A substantial excess of anhydride should be used, preferably about 10 moles of anhydride per mole of hydroxy compound reactant. The excess anhydride serves as a reaction diluent and solvent. The reaction is preferably carried out in the range of about 0° to 75° C, or higher, usually from about 10 minutes to 36 hours. The acylated product is isolated from the reaction by conventional methods. For example, the excess anhydride can be decomposed with water, and the resulting mixture acidified and then extracted with a solvent, and the acylate recovered by evaporation. If desired, the acylate can be purified by conventional methods, such as chromatography.

Examples of suitable anhydrides are acetic anhydride, propionic anhydride, butyric anhydride, acrylic anhydride, crotonic anhydride, benzoic anhydride and the like. Optionally, suitable acid halides can also be used, such as acetyl chloride, propionyl chloride, butyryl chloride, isobutyryl chloride, succinyl chloride, furoyl chloride and the like.

The hydroxyl group attached to a nonnutritive flavor imparting compound, a polymer or an intermediate can optionally be etherified to form ether derivatives that have desirable solubilities in various media, carriers, foods, beverages and medicines. One method of preparing the ether is comprised of contacting a free hydroxyl group with an alkali hydroxide in an organic solvent to form the alkoxide. The alkoxide is then contacted with an alkyl iodide yielding the corresponding alkyl ether. Generally, the reaction is carried out at 5° to 150° C for about 15 minutes to 24 hours and optionally in the presence of a catalyst such as cuprous chloride to quicken the reaction. The ether is recovered from the reaction medium by standard techniques such as extraction, evaporation, etc. Typical of the alkyl iodides suitable for the reaction include ethyl iodide, isopropyl iodide, cyclohexylmethyl iodide, methyl iodide, 1-butyl iodide, and the like.

The following examples are set forth as representative methods illustrative of the spirit of the present invention. These examples are not to be construed as limiting the scope of the invention as other functionally equivalent means will be readily apparent to those skilled in the subject art.

EXAMPLE 1

First, the naturally occurring phenol eugenol,

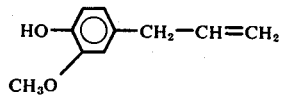

is epoxidized with 2 equivalents of m-chloroperbenzoic acid in methylene chloride at room temperature for about 50 hours to yield the corresponding epoxide

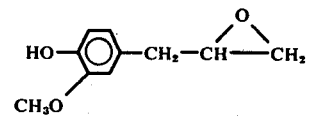

Next, the freshly prepared epoxide is copolymerized with an excess of ethylene oxide under conventional Lewis acid conditions, such as in the presence of $BF_3 \cdot Et_2O$ for 1 hour at 70° C, Chemical Abstracts, Vol. 71, 50660b, 1969, to yield the polymeric flavor modifier (spicy) of the structure

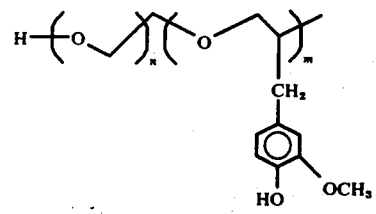

wherein $n$ is greater than $m$ and $n$ and $m$ are from 10 to 10,000.

EXAMPLE 2

A novel compound of the invention is prepared as follows: the esterification of 5-methoxysalicylic acid is accomplished with an excess of methanol containing a small amount of sulfuric acid. The resulting methyl ester

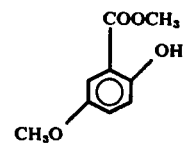

is converted to its sodium salt by treatment with one equivalent of sodium hydride in dry glyme with alkylation of the phenol salt

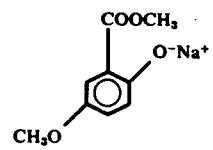

with pentanol at reflux temperature for 20 hours to yield the primary alcohol

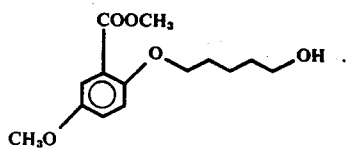

The latter alcohol next is converted into its acetal

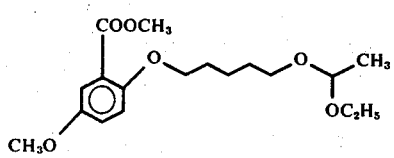

derivative on treatment with a large excess of ethyl vinyl ether in the presence of a trace of p-toluenesulfonic acid. The acetal is converted to the related vinyl ether

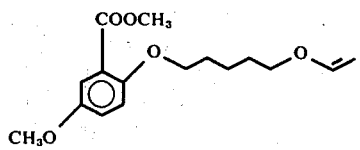

by heating the acetal in the presence of alumina, $Al_2O_3$, and distillation of the ethanol formed by thermal elimination. Copolymerization of the aromatic vinyl ether with maleic anhydride in the presence of benzoyl peroxide leads to the polymeric anhydride

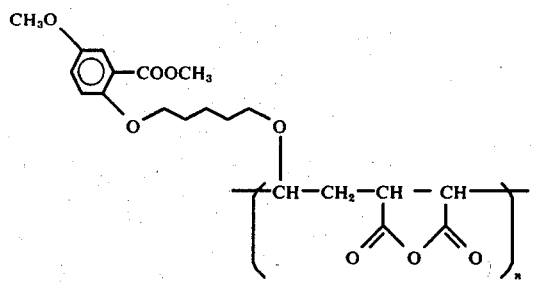

which is converted to the polymeric carboxylic acid flavor modifier on treatment with dilute acid at room temperature to yield the following compound wherein $n$ is greater than 10.

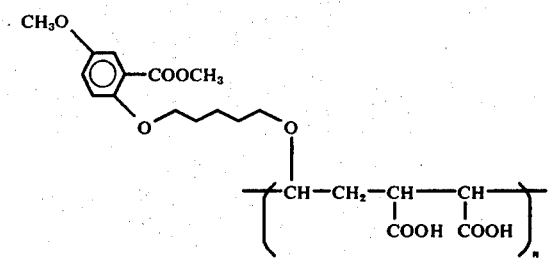

EXAMPLE 3

The covalent bonding of a biologically active flavoring agent to a polymer to give $(F-Z)_n-C$ can also be carried out according to the invention as follows: to 1.5 moles of ethylene glycol of the structural formula

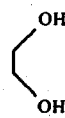

in 1 liter of toluene containing a trace of p-toluene sulfonic acid,

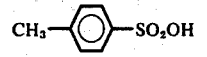

is added 1 mole vanillin

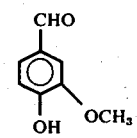

and the resulting water formed by azeotropic distillation to give

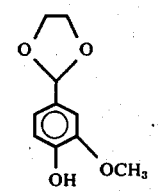

Next, 1 mole of the acetal is added to 1.0 moles of NaOH in 2 liters of n-propanol followed by the addition of 1.25 moles of 4-bromobutanoic acid sodium salt, Br COO⁻Na and the resulting mixture refluxed for 24 hours to yield

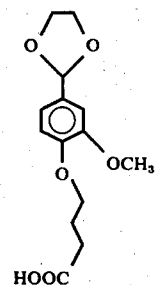

after cooling and acidification to pH 4. The acid is next converted to the acid chloride by adding dropwise to 1 mole of the acid stirred into 1 liter of benzene containing 1.1 moles of pyridine 1 mole of oxalyl chloride $(COCl)_2$ with the reaction proceeding with continual stirring at 20° C for 5 hours to yield

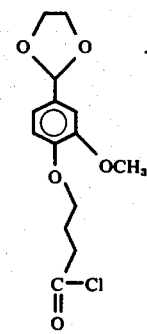

Next, 1 mole of the acid chloride is added to 1 liter of pyridine containing 1 to 10 moles of polyvinyl alcohol for each mole of acid chloride and the esterification carried out at 80° C. The product is recovered by pouring the reaction mixture into acetone containing 200 ml of 0.1N HCl and stirred for 5 hours then washed several times with excess acetone, and dried over calcium chloride in a desiccator to yield

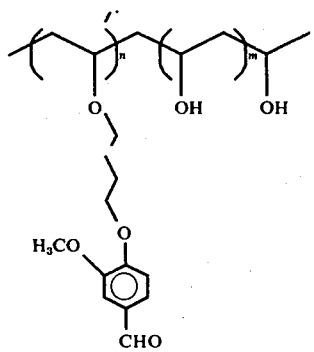

wherein the ratio of n to m varies from 1:1 to 1:10.

EXAMPLE 4

To 1 mole of sodium hydroxide stirred into 1 liter of n-propanol is slowly added with continual stirring 1 mole of methyl p-hydroxybenzoate, and the mixing carried out for an additional hour at room temperature. Next, this mixture is added to a reaction mixture comprising 1.1 mole of the sodium salt of Br∧∧∧CH₂OH 4-bromobutanoic acid in one liter of n-propanol and the mixture of the reactants refluxed for about 18 hours under atmospheric pressure. The solvent is next evaporated on a conventional rotary evaporator to give the ether of the formula

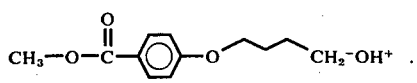

The primary alcohol is converted into its tosylate derivative

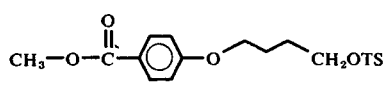

by means of an excess (2 equivalents) of freshly crystallized p-toluenesulfonyl chloride in dry pyridine at 0° for 12 hours. The resulting crystalline tosylate is then alkylated at room temperature with polyvinyl alcohol in dry dimethyl sulfoxide containing from 0.1 to 1.0 equivalents of dimsyl anion

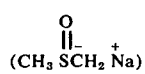

followed by precipitation of the desired polymeric flavor modifier

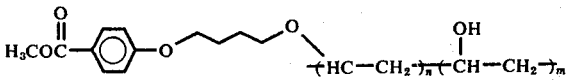

by pouring the reaction mixture into methanol and washing the solid material with an excess of methanol. In the above formula $m$ is equal to or greater than $n$ and $m$ and $n$ are 10 to 100,000.

EXAMPLE 5

To 1 liter of pyridine containing 4 moles of p-toluenesulfonyl chloride is slowly added with medium stirring 1 mole of poly(ethyleneglycol)—HO(CH₂CH₂O)$_n$H and the reactants allowed to react for 4 hours at 25° C and under normal atmospheric pressure, to give the poly(ethyleneglycol) tosylate. The latter compound is then subjected to displacement reaction by adding the tosylate to a reaction vessel containing 3.5 moles of sodium iodide that had been previously stirred into 1.5 liters of dry acetone and heating under reflux for 10 hours to from the poly(ethyleneglycol) iodide. To a separate reaction flask containing 2.3 moles of ethyleneglycol HO⌒OH, 500 mg of the acid catalyst p-toluenesulfonic acid in 3 liters of benzene is added 2 moles of p-hydroxybenzaldehyde

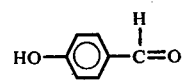

and the reaction carried out with the azeotropic distillation of water to give the hemiacetal

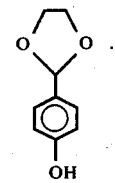

Next, to a boro-silicate reaction vessel containing 2 moles of sodium hydroxide in 4 liters of n-propanol is added 1 mole of the previously prepared poly(ethyleneglycol)iodide and the reactants refluxed for 10 hours to form

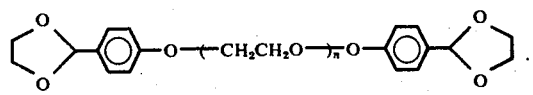

The latter acetal is then hydrolyzed with 0.1 N HCl for 5 hours at 50° C and the fruit flavor enhancer recovered by pouring the reaction into a large excess of tetrahydrofuran to precipitate the polymer of the structure

wherein $n$ varies from 10 to 150,000.

The nonnutritive, nonabsorbable flavor imparting compounds of the invention (F—Z)$_n$—C are useful for enhancing, modifying, or imparting flavor and flavor-like effects to various orally acceptable substances. Flavor, as used herein, is generically the effect perceived by the senses as the resulting action of flavor, flavor-like, flavor modifiers, enhancers, or flavor imparting ingredients. Flavor further comprises the product of a physiological reaction, such as the pure, basic responses, usually classified as the primary tastes comprising, bitter, salty and sour. The term flavor also comprises for the purpose of the invention taste qualities such as metallic, alkaline, soapy, astringent, tart, spicy, fruit, vegetable, nutty, dough, cheese, metallic, oily, beverage, extracts, meat, fish, poultry, unprocessed food, prepared foods, creamy, confectionary, medicinal, natural, artificial, liquor, wine, mixtures thereof and the like.

The nonabsorbable, nonnutritive flavor imparting compounds $(F-Z)_{\overline{n}}-C$ of the invention can be taken singly or admixed in various proportions with like and unlike substances. The novel flavor compounds can be taken into the oral cavity alone, or they can be taken into the digestive tract of animals including humans, farm animals, sport and household animals, zoo animals, laboratory animals, avians and fish to produce a predetermined flavor response without any direct or indirect unwanted or adverse effects. The compounds of the invention can be mixed with liquids and solids, precooked and cooked comestibles, fresh and frozen products in an amount sufficient to give a flavor imparting effect to the user. They can be admixed with substances that are used orally for a short period of time such as chewing gum, toothpaste, oral cosmetics, mouthwash, tobacco products, and the like. The nonabsorbable, nonnutritive flavor imparting agents, $(F-Z)_{\overline{n}}-C$, can be admixed with liquids that are retained for a prolonged period of time in the gastrointestinal tract, such as coffee, tea, cola, fruit extracts, sweet milk, chocolate milk, and the like.

The nonabsorbable, nonnutritive compounds $(F-Z)_{\overline{n}}-C$, can also be incorporated into any of a wide variety of foods, including baked goods such as crackers, bread, pretzels, pastries, pies, cakes and the like; milk products such as ice cream, sherberts, custards and assorted puddings; gelatin products; cereal products; processed canned fruits, vegetables and juices, frozen vegetables; meat products such as cured bacon and ham; beverages such as soft drinks; and the like. The compounds can also be added to confectionary products such as candies, jellybeans, taffy, chocolate bars, licorice, divinity and the like. The nonnutritive, nonabsorbable flavor impartors $(F-Z)_{\overline{n}}-C$ can be added to farm feeds such as silage, premixes, mash, pet snacks and the like. Also, they can be added to laboratory animal feeds that are manufactured into pellets, and other conventional forms of feeds. The new and useful flavor imparting compounds can also be combined with medicinals and pharmaceutical formulations including tablets, capsules, powders, lozenges, drops, elixirs, syrups, suspensions, oils, emulsions, and the like.

The products of this invention were water soluble. That is they will dissolve in water and water containing edibles to an extent of at least 50 parts per million, preferably to an extent of at least about 100 parts per million, bases water or edible material.

The amount of flavor imparting compound $(F-Z)_{\overline{n}}-C$ to be used is not critical so long as an effective amount is used. Usually this is an amount which provides a preselected flavor or taste comparable to naturally occurring or a corresponding synthetic product. The amount used will vary for a particular host or ingredient, and it will usually range from 0.001 percent to 10 percent, more or less of the total weight of the composition containing same. Generally, the amount used will vary for a particular host or ingredient, and it will usually range from 0.01 p.p.m., wherein p.p.m. is parts per million, to 25,000 p.p.m., or higher based on the weight of an orally acceptable comestible substance to which they are added. By comestible substance is meant those orally acceptable substances described above such as food, beverage, confection, medicine and the like. The novel compounds can also be used alone or in combination with any of the other compounds of the invention in an effective amount for stimulating a sensory receptor to give a response.

Additionally, the novel flavor imparting compounds $(F-Z)_{\overline{n}}-C$ of the invention can be mixed with other agents including thickeners such as alginates, carrageenin and the like to impart a body to gravies; they can be mixed with condiments such as spices and salts including pepper, allspice, basil, capsicum extract, cloves, eugenol, garlic oil, onion oil, oregano extract, sage oil, sodium citrate, thyme, hydrolyzed vegetable protein and the like. The flavoring imparting compounds $(F-Z)_{\overline{n}}-C$ can be used as encapsulating agents so that the flavor imparting compounds can be coacervated to provide microencapsulated products.

Comestible compositions of matter are prepared according to the mode and manner of the invention by using the nonnutritive, nonabsorbable flavor imparting compounds in conventional ways. For example, an ice cream is prepared from ice cream forming ingredients such as cream, yolk of eggs, any of the flavor imparting agents of the invention, and other ingredients by processing the ice cream forming ingredients in the usual manner in an ice cream machine. Similarly, a milk pudding comprised of starch, salt, milk, the novel flavor imparting compounds, triacetin and other optional ingredients is prepared by cooking and solififying the resulting pudding in the conventional manner. The novel and useful flavor imparting compounds can be used in other foods or beverages comprised of other food forming ingredients such as edible oils, milk solids, shortening, cocoa, butter propylene glycol disterate, bulking agents and the like, as a flavor imparting agent wherever flavor and taste imparting agents were used heretofore. For example, a chicken flavor imparting composition is prepared by mixing vegetable shortening, salt, glutamic acid, L-cystemic hydrochloride, glycine, alanine, taurine, disodium guanylate, disodium inosinate and alkyl thiazole derivative covalently bonded to a water soluble polymer to give a chicken flavor imparting composition of matter. Other compositions are suitably prepared by those skilled in the art and this disclosure embraces within its scope all like compositions.

The nonnutritive, nonabsorbable artifical flavor imparting compounds $(F-Z)_{\overline{n}}-C$ of the invention are distinct from naturally occurring flavors because they are not metabolized to yield carbon dioxide, water and energy while retaining their flavor producing properties. Additionally, they do not have an insulin requirement, and they do not age as naturally occurring flavors do during the processing of foods. Also, since the active flavor imparting group is joined to a means for transporting it to yield its effect, while preventing its absorption and assimilation, any adverse effects inherent in the active group is retained by the entire compound for eventual elimination from the gastrointestinal tract. And, while the above examples and disclosure are set forth merely for illustrating the mode and manner of the invention, various modifications and embodiments can be made by those skilled in the art in the light of the invention without departing from the spirit of the invention.

What is claimed is:

1. A method for imparting a flavor to an edible comestible comprising adding thereto an effective amount of a nonnutritive, nonabsorbable, water soluble flavor imparting compound comprising an active flavoring agent bound through a bondable position that is not essential for its flavor imparting activity with a biologically nonrupturable covalent bond that maintains its physical and chemical integrity under primary gastrointestinal digestive conditions to a polymeric nonmetabolizable nonbiodegradable controller molecule having a molecular weight in excess of 400 and dimensions such that the compound has a molecular weight in excess of 1000 and dimensions that essentially prevent the active and passive absorption of the compound from the mucosal to the serosol side of the gastrointestinal tract of a warm blooded host as the compound passes through said gastrointestinal tract.

2. A comestible composition of matter comprising an essentially nonabsorbable, nonnutritive, water soluble flavor imparting compound of the general formula $(F-Z)_{\overline{n}}-C$ wherein F is a biologically active flavor imparting agent, Z is a covalent bond that permanently bonds the flavor imparting agent to C and is essentially unaltered under the conditions of passage through the gastrointestinal tract, $n$ is at least one, and C is a polymeric controller molecule other than F that is substantially indigestible and non-absorbable and has a molecular weight in excess of 400 and a three dimensional space occupying group of molecular dimensions that prevent $(F-Z)_{\overline{n}}-C$ absorption through the mucosa of the gastrointestinal tract as the flavor imparting compound passes through the gastrointestinal tract, and wherein the flavor imparting compound is admixed with an edible comestible substance.

3. A comestible composition according to claim 1 wherein the composition contains from 0.001 percent to 10 percent of the essentially nonabsorbable, nonnutritive flavor imparting compound based on the total weight of the comestible substance.

* * * * *

UNITED STATES PATENT OFFICE
CERTIFICATE OF CORRECTION

Patent No. 3,998,974    Dated Dec. 21, 1976

Inventor(s) Alejandro Zaffaroni

It is certified that error appears in the above-identified patent and that said Letters Patent are hereby corrected as shown below:

The term of this patent subsequent to April 4, 1992 has been disclaimed.

Signed and Sealed this

First Day of March 1977

[SEAL]

Attest:

RUTH C. MASON
Attesting Officer

C. MARSHALL DANN
Commissioner of Patents and Trademarks